United States Patent
Luo et al.

(10) Patent No.: US 10,954,245 B2
(45) Date of Patent: Mar. 23, 2021

(54) THERMAL ACTIVE DELAY FLUORESCENT MATERIAL, METHOD FOR MANUFACTURING SAME, AND ORGANIC LIGHT-EMITTING DIODE DEVICE

(71) Applicant: WUHAN CHINA STAR OPTOELECTRONICS SEMICONDUCTOR DISPLAY TECHNOLOGY CO., LTD., Hubei (CN)

(72) Inventors: Jiajia Luo, Hubei (CN); Xianjie Li, Hubei (CN); Yu Gu, Hubei (CN); Jinchang Huang, Hubei (CN); Xu Wang, Hubei (CN)

(73) Assignees: WUHAN CHINA STAR OPTOELECTRONICS, Hubei (CN); SEMICONDUCTOR DISPLAY TECHNOLOGY CO., LTD., Hubei (CN)

( * ) Notice: Subject to any disclaimer, the term of this patent is extended or adjusted under 35 U.S.C. 154(b) by 106 days.

(21) Appl. No.: 16/489,454

(22) PCT Filed: May 6, 2019

(86) PCT No.: PCT/CN2019/085642
§ 371 (c)(1),
(2) Date: Aug. 28, 2019

(87) PCT Pub. No.: WO2020/211126
PCT Pub. Date: Oct. 22, 2020

(65) Prior Publication Data
US 2020/0331923 A1    Oct. 22, 2020

(30) Foreign Application Priority Data
Apr. 16, 2019 (CN) .......................... 201910305494.7

(51) Int. Cl.
*C07D 487/14* (2006.01)
*H01L 51/50* (2006.01)
(Continued)

(52) U.S. Cl.
CPC .......... *C07D 487/14* (2013.01); *H01L 51/001* (2013.01); *H01L 51/0003* (2013.01);
(Continued)

(58) Field of Classification Search
CPC . C07D 487/14; H01L 51/0003; H01L 51/001; H01L 51/0072; H01L 51/0094; H01L 51/5088
(Continued)

(56) References Cited

U.S. PATENT DOCUMENTS

2018/0053903 A1* 2/2018 Suzuki etal. ........ H01L 51/0071
428/690

* cited by examiner

*Primary Examiner* — Thinh T Nguyen

(57) ABSTRACT

A thermal active delay fluorescent material includes a structural formula in formula 1:

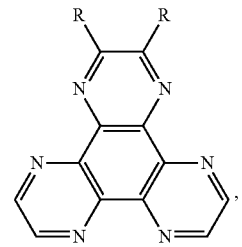

formula 1 wherein in the formula 1, R is a chemical group of an electron donor.

The application adopts a strong electron-withdrawing group of a large conjugate plane as an electron acceptor, and
(Continued)

combines an electron acceptor with a strong electron donor to achieve a deep red light thermal active delay fluorescent material with a typical TADF characteristics and a low energy level. The thermal active delay fluorescent material of the application is a deep red light TADF material having a lower single triplet energy level difference, an ultrafast reverse intersystem crossing speed and a high luminous efficiency, and when it is used as a luminescent material for an organic light-emitting diode device, it can promote a luminous efficiency of the organic light-emitting diode device.

10 Claims, 2 Drawing Sheets

(51) Int. Cl.
     *H01L 51/00*      (2006.01)
     *H01L 51/52*      (2006.01)

(52) U.S. Cl.
     CPC ...... H01L 51/0072 (2013.01); H01L 51/0094 (2013.01); *H01L 51/5012* (2013.01); *H01L 51/5056* (2013.01); *H01L 51/5088* (2013.01); *H01L 51/5218* (2013.01); *H01L 2251/53* (2013.01)

(58) Field of Classification Search
     USPC .............................................. 257/40; 428/690
     See application file for complete search history.

THERMAL ACTIVE DELAY FLUORESCENT MATERIAL, METHOD FOR MANUFACTURING SAME, AND ORGANIC LIGHT-EMITTING DIODE DEVICE

CROSS REFERENCE TO RELATED APPLICATION

This application claims the priority of International Application No. PCT/CN2019/085642, filed on 2019 May 6, which claims priority to Chinese Application No. 201910305494.7, filed on 2019 Apr. 16. The entire disclosures of each of the above applications are incorporated herein by reference.

BACKGROUND OF INVENTION

Field of Invention

The present invention relates to an electroluminescent material field, and particularly to a thermal active delay fluorescent material, a method for manufacturing the thermal active delay fluorescent material, and an organic light-emitting diode device.

Description of Prior Art

Organic light-emitting diode (OLED) display panels have attracted attentions of many researchers by active illumination without a backlight, high luminous efficiency, wide viewing angles, fast response speed, large temperature adaptation range, relatively simple production and processing technology, low drive voltage, low energy consumption, lighter and thinner, flexible display, and huge application prospects.

The principle of the OLED device is that, under the action of an electric field, holes and electrons are injected from an anode and an cathode, respectively, and through a hole injection layer, a hole transport layer, an electron injection layer, and an electron transport layer recombined to generate excitons in a light emitting layer, and the excitons radiation attenuates to emit light.

As a core component of OLED devices, organic electroluminescent materials have a great influence on the performance of devices. The light emitting layer of an OLED device generally contains a subject material and an object material, of which the luminescent object material is critical. The luminescent object materials used in early OLED devices were fluorescent materials, because of the 1:3 ratio of singlet and triplet excitons of which in OLED devices, the theoretical internal quantum efficiency (IQE) of OLED devices based on fluorescent materials only can reach 25%, which greatly limits applications of fluorescent electroluminescent devices. The heavy metal complex phosphorescent material can achieve 100% IQE by using singlet and triplet excitons simultaneously due to the spin-orbit coupling of heavy atoms. However, the heavy metals commonly used are precious metals such as iridium (Ir), platinum (Pt), and etal, and heavy metal complex phosphorescent materials have yet to be broken in terms of blue light materials. Pure thermal active delay fluorescent (TADF) material with a molecular structure combining electron donor (D) and electron acceptor (A). The molecular design has a small lowest single triple energy level difference ($\Delta E_{ST}$), such triplet excitons can return to the singlet state through the reverse intersystem crossing (RISC), and then illuminate by the radiation transition to the ground state, so that single and triplet excitons can be simultaneously utilized to achieve 100% IQE.

For TADF materials, fast reverse intersystem crossing constants ($k_{RISC}$) and high photoluminescence quantum yield (PLQY) are necessary for the fabrication of high efficiency OLED devices. At present, TADF materials with the above conditions are still relatively scarce compared with heavy metal Ir complexes, and heavy metal complex phosphorescent materials have yet to be broken in the field of deep red light. Therefore, it is particularly important to develop high-performance deep red light TADF materials.

SUMMARY OF INVENTION

A purpose of the application is that to provide a thermal active delay fluorescent material with an ultrafast reverse intersystem crossing speed and a high luminous efficiency, which has a typical TADF characteristics and is a deep red light TADF material with a low energy level, and can be used as a light emitting layer material of an organic light-emitting diode device.

Another purpose of the application is that to provide a method for manufacturing a thermal active delay fluorescent material, the method is easy to control and to achieve a product with a high yield.

Another purpose of the application is that to provide an organic light-emitting diode device, a luminous efficiency of the device is promoted by a thermal active delay fluorescent material used as a light emitting layer material.

In order to achieve the above purposes, the application provides a thermal active delay fluorescent material with a structural formula in formula 1:

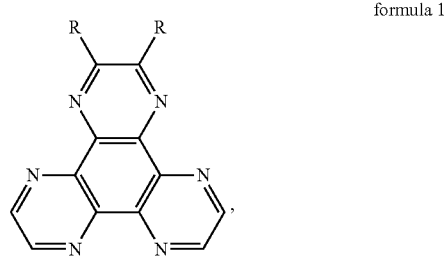

formula 1 wherein in the formula 1, R is a chemical group of an electron donor.

The chemical group R of the electron donor is one of:

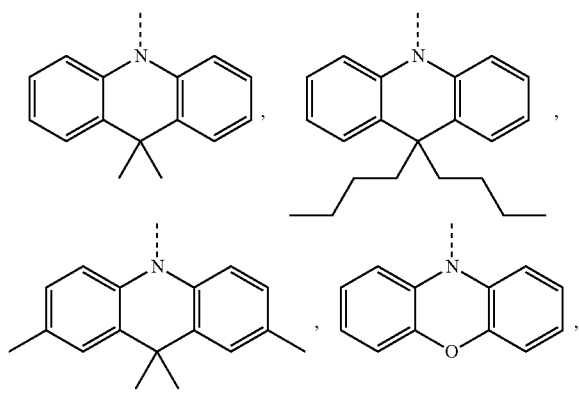

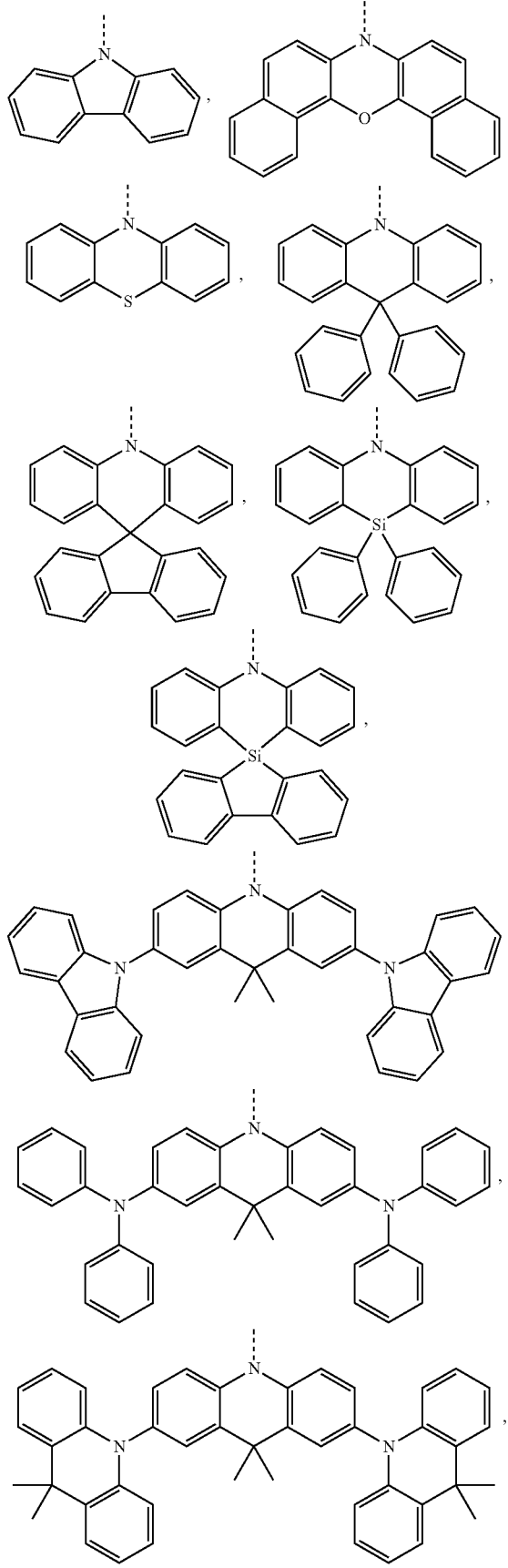
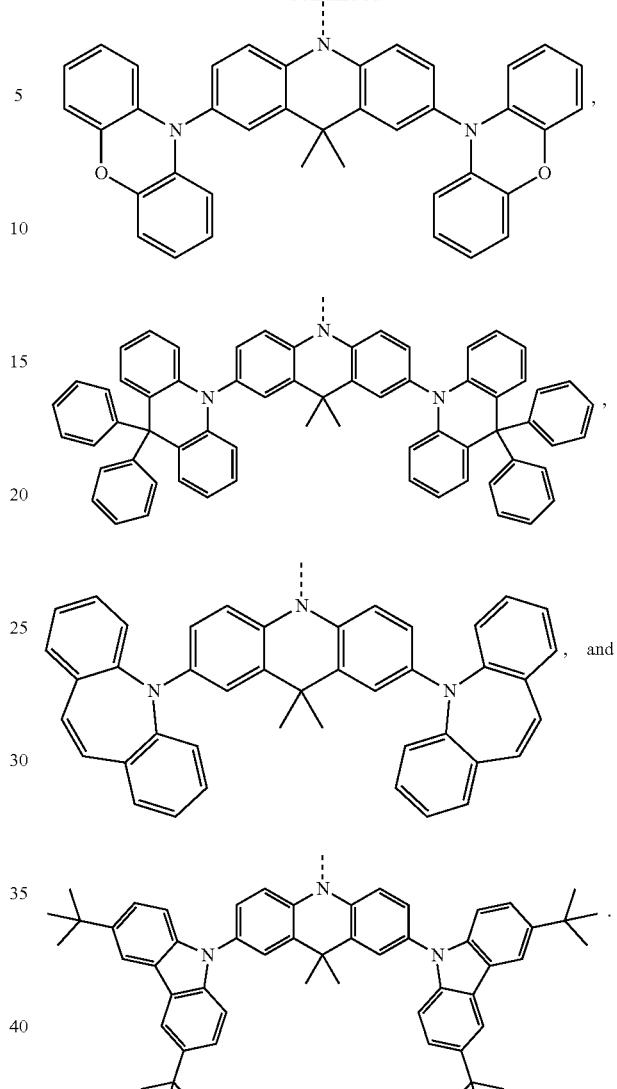
The thermal active delay fluorescent material is a compound 1, a compound 2, or a compound 3, structural formulas of the compound 1, the compound 2, and the compound 3 are defined as:
compound 1
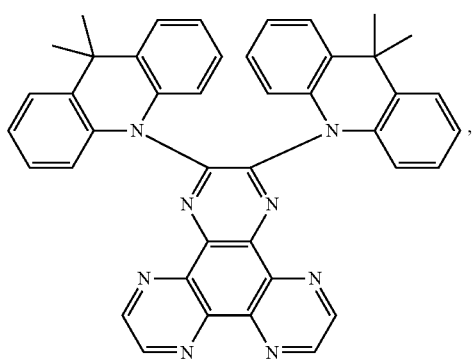

compound 2

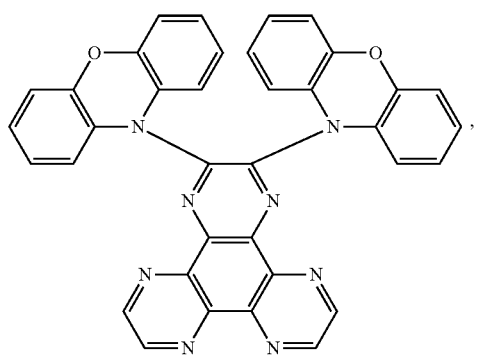, compound 3

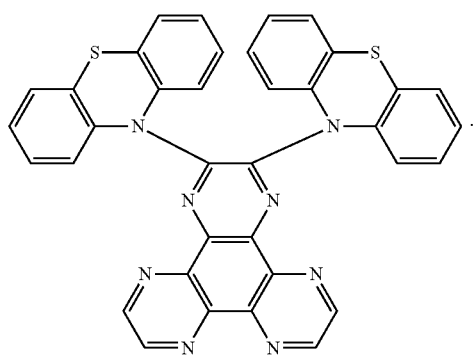.

The application also provides a method for manufacturing a thermal active delay fluorescent material, wherein a chemical equation is:

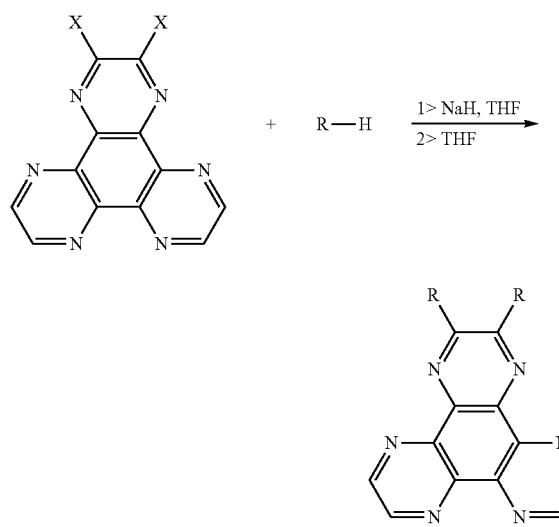

wherein a compound with an electron donor is added into a container, NaH is added into the container in an anhydrous and oxygen-free environment, dehydrogenation and deoxygenation of tetrahydrofuran is added into the container in an argon atmosphere, those are reacted at 55° C.-65° C. for 1.5-2.5 hours, and a halogenated material is added into the container, and then those are reacted at 55° C.-65° C. for 20-30 hours, wherein a molar ratio of the halogenated material, the compound with the electron donor, and NaH is 1:2-4:2-4; after the reaction is completed, the reacted liquid is cooled to room temperature, poured into ice water, after a extraction process, an organic phase is collected, which is separated into silica gel, purified by a column chromatography to obtain a product, and to calculate a yield;

wherein a structural formula of the halogenated material is

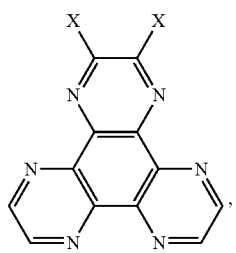, and X is a halogen group;

a structural formula of the compound with the electron donor is R—H, and R is a chemical group of the electron donor.

The structural formula of the halogenated material is

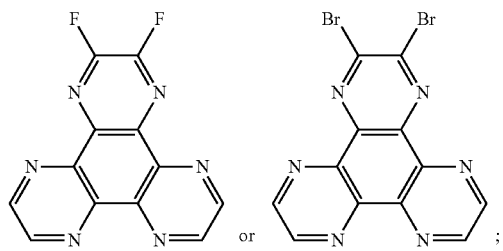;

the chemical group R of the electron donor is one of:

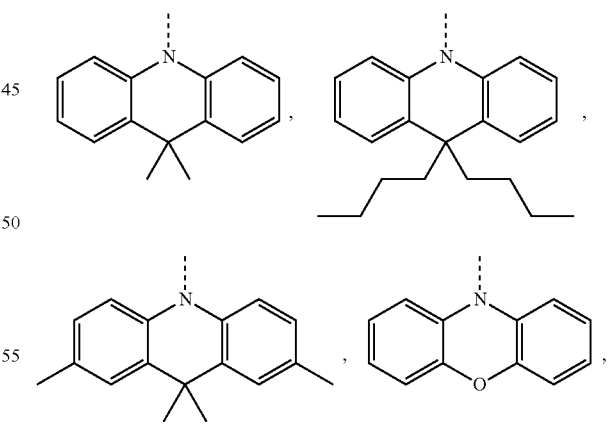

-continued

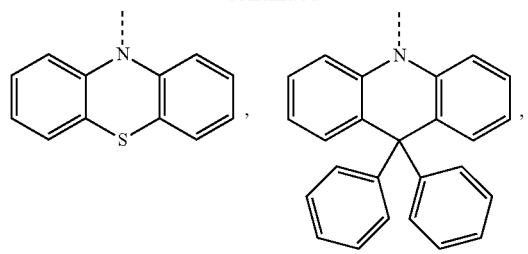

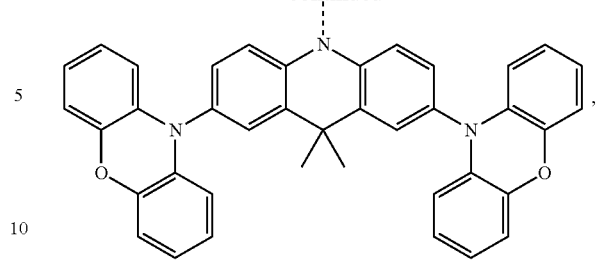

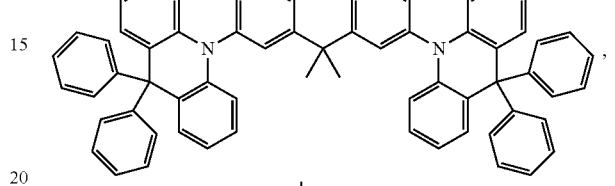

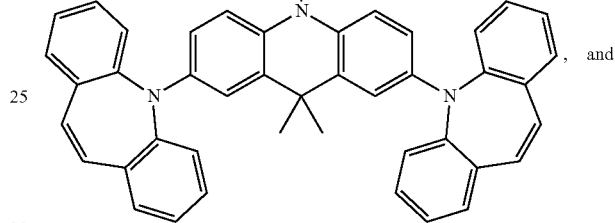

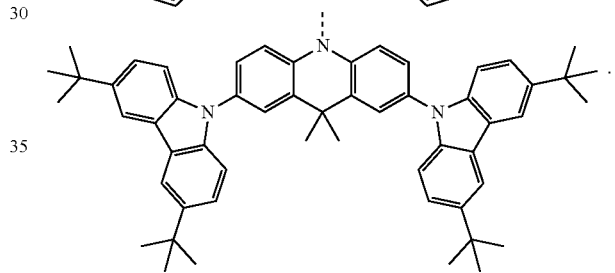, and

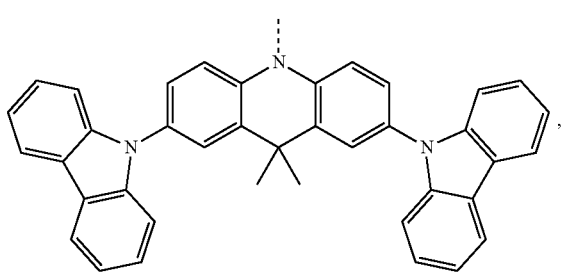

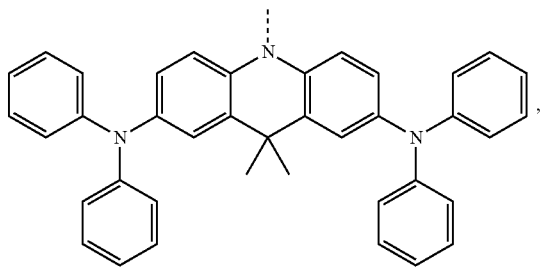

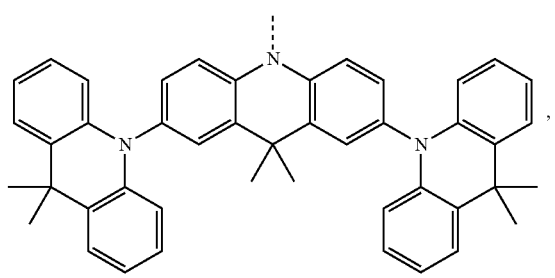

The compound with the electron donor is 9,10-dihydro-9,9-dimethyl acridine, phenoxazine, or phenothiazine.

The application also provides an organic light-emitting diode device including a substrate, a first electrode formed on the substrate, an organic functional layer formed on the first electrode, and a second electrode formed on the organic functional layer;

wherein the organic functional layer comprises one layer or several layers of organic film layers and at least one layer of the organic film layer is a light emitting layer;

the light emitting layer comprises a thermal active delay fluorescent material of the above.

The light emitting layer is manufactured by a vacuum evaporation process or a coating solution process.

A material of the light emitting layer is a mixture of a subject material and an object material, the object material is selected one or several from the thermal active delay fluorescent material of the above.

The substrate is a glass substrate, a material of the first electrode is indium tin oxide, the second electrode is a double layer composite structure of a lithium fluoride layer and an aluminum layer;

the organic functional layer comprises several layers of the organic film layers, the several layers of the organic film layers comprises a hole injection layer, a hole transport layer, a luminescence layer, and an electron transport layer, wherein a material of the hole injection layer is 2,3,6,7,10,11-hexacyano-1,4,5,8,9,12-hexaazatriphenylene (HATCN), a material of the hole transport layer is 4,4′,4″-tris(carbazol-9-yl)-triphenylamine (TCTA), a material of the electron transport layer is 1,3,5-tri[(3-pyridyl)-phen-3-yl]benzene (TmPyPB), and the subject material is 3,3′-Bis(N-carbazolyl)-1,1′-biphenyl (mCBP).

Compared with materials and technologies of the prior art, the advantages and benefits of the present application are:

(1) The application adopts a strong electron-withdrawing group of a large conjugate plane as an electron acceptor, and combines an electron acceptor with a strong electron donor to achieve a deep red light thermal active delay fluorescent material with a typical TADF characteristics and a low energy level;

(2) The thermal active delay fluorescent material of the application is a deep red light TADF material having a lower single triplet energy level difference, an ultrafast reverse intersystem crossing speed and a high luminous efficiency, and when it is used as a luminescent material for an organic light-emitting diode device, it can promote a luminous efficiency of the organic light-emitting diode device, the organic light-emitting diode device with the deep red light thermal active delay fluorescent material of the application achieves a very high device efficiency.

BRIEF DESCRIPTION OF DRAWINGS

The technical solutions and other advantageous effects of the present invention will be apparent from the following detailed description of embodiments of the invention.

DETAILED DESCRIPTION OF PREFERRED EMBODIMENTS

Figure 1:
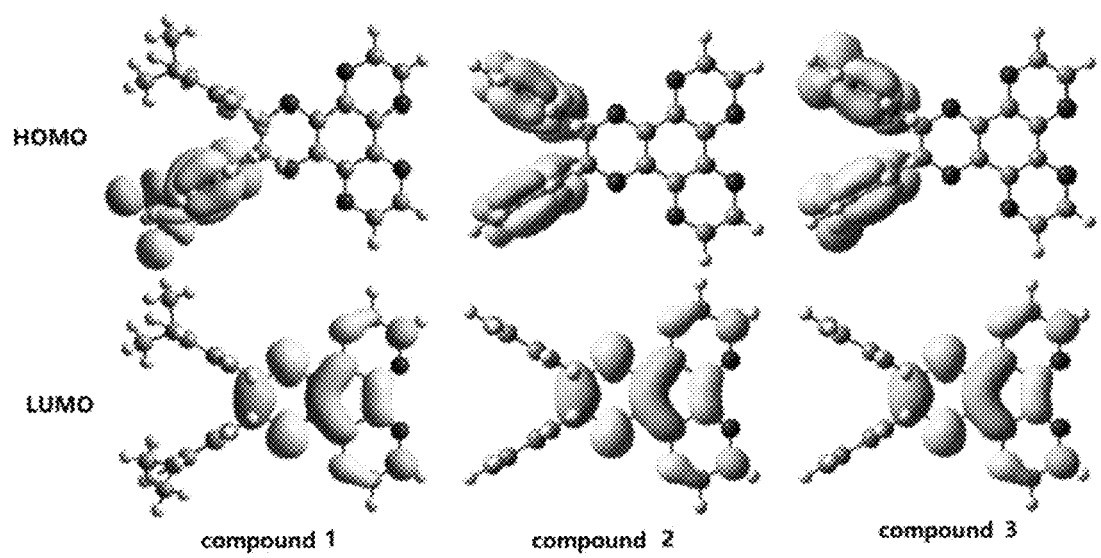
FIG. 1 is a highest occupied molecular orbital (HOMO) and lowest unoccupied molecular orbital (LUMO) energy level distribution spectrum of compounds 1-3 manufactured by exemplary embodiments 1-3 of the application.

Some of the unspecified raw materials used in the present invention are commercially available products. The preparation of some compounds will be described in the examples. The present invention will be further described in detail below with reference to specific embodiments, but the embodiments of the present invention are not limited thereto.

Embodiment 1

A synthesis route of a compound 1 is as followed:

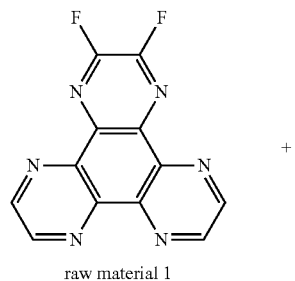

raw material 1

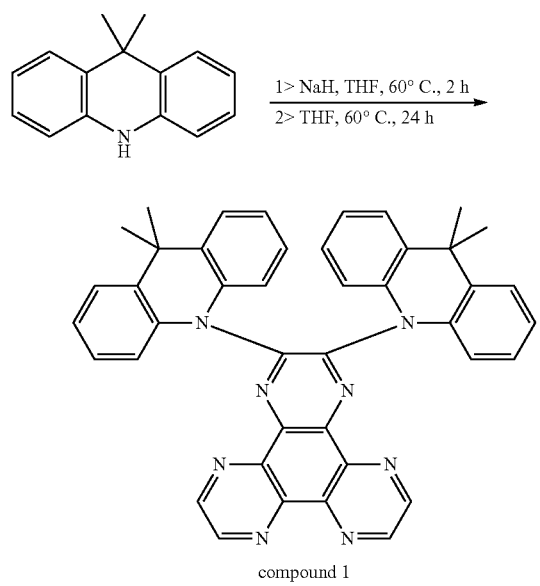

compound 1

9,10-dihydro-9,9-dimethyl acridine (2.51 g, 12 mmol) is added into a 100 mL two neck bottle, NaH (0.48 g, 12 mmol) is added by a glove box, dehydrogenation and deoxygenation of 40 mL tetrahydrofuran (THF) is added in an argon atmosphere, those are reacted at 60° C. for 2 hours, and the raw material 1 (5 mmol, 1.35 g) is added, and then those are reacted at 60° C. for 24 hours. The reacted liquid is cooled to room temperature, poured into 200 mL ice water, and extracted three times with dichloromethane, an organic phase is collected, which is separated into silica gel, purified by a column chromatography (dichloromethane:n-hexane v:v, 3:2) to obtain 2.4 g orange powders, and a yield is 62%.

1HNMR (300 MHz, $CD_2Cl_2$, δ): 8.74 (s, 4H), 7.19-7.14 (m, 12H), 6.98-6.93 (m, 4H), 1.69 (s, 12H).

MS (EI) m/z: [M]$^+$ calcd for $C_{42}H_{32}N_8$, 648.27; found, 648.18.

Embodiment 2

A synthesis route of a compound 2 is as followed:

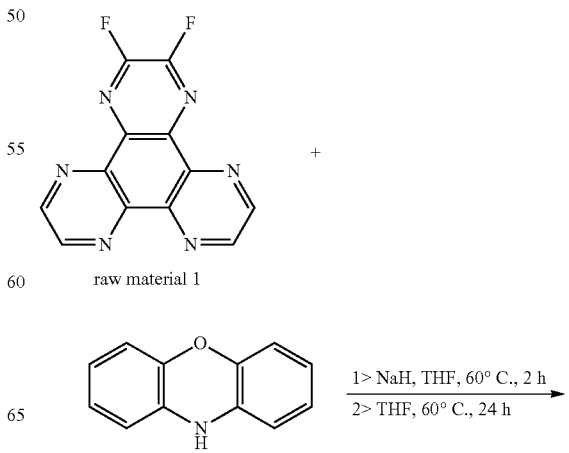

raw material 1

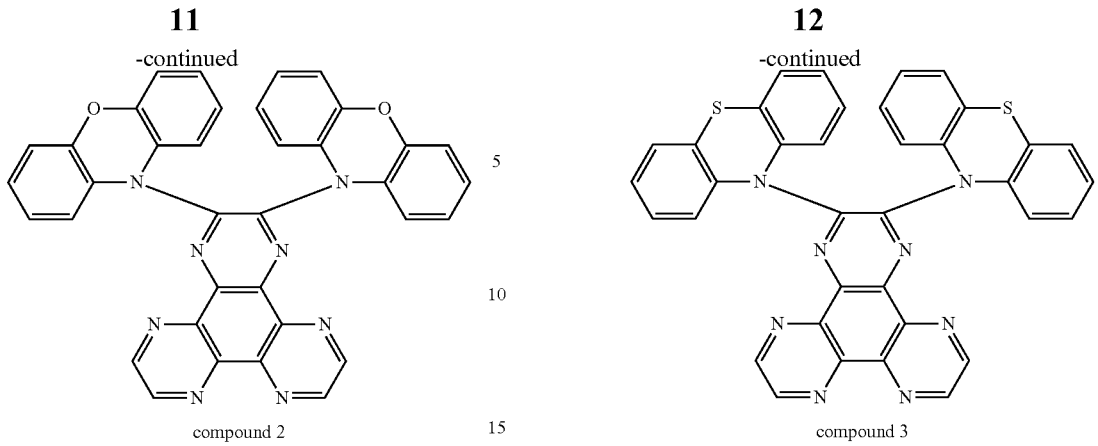

compound 2 compound 3

Phenoxazine (2.20 g, 12 mmol) is added into a 100 mL two neck bottle, NaH (0.48 g, 12 mmol) is added by a glove box, dehydrogenation and deoxygenation of 40 mL tetrahydrofuran (THF) is added in an argon atmosphere, those are reacted at 60° C. for 2 hours, and the raw material 1 (5 mmol, 1.35 g) is added, and then those are reacted at 60° C. for 24 hours. The reacted liquid is cooled to room temperature, poured into 200 mL ice water, and extracted three times with dichloromethane, an organic phase is collected, which is separated into silica gel, purified by a column chromatography (dichloromethane:n-hexane v:v, 3:2) to obtain 1.9 g red powders, and a yield is 64%.

$^1$HNMR (300 MHz, $CD_2Cl_2$, δ): 8.74 (s, 4H), 7.14-7.06 (m, 4H), 7.01-6.95 (m, 12H).

MS (EI) m/z: $[M]^+$ calcd for $C_{36}H_{20}N_8O_2$, 596.17; found, 596.16.

Embodiment 3

A synthesis route of a compound 3 is as followed:

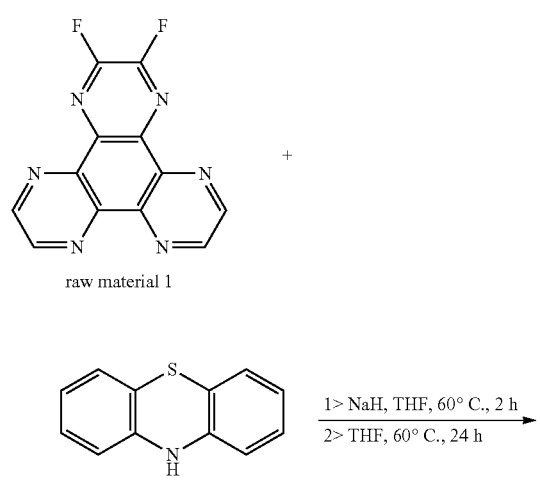

raw material 1

1> NaH, THF, 60° C., 2 h
2> THF, 60° C., 24 h

Phenothiazine (2.39 g, 12 mmol) is added into a 100 mL two neck bottle, NaH (0.48 g, 12 mmol) is added by a glove box, dehydrogenation and deoxygenation of 40 mL tetrahydrofuran (THF) is added in an argon atmosphere, those are reacted at 60° C. for 2 hours, and the raw material 1 (5 mmol, 1.35 g) is added, and then those are reacted at 60° C. for 24 hours. The reacted liquid is cooled to room temperature, poured into 200 mL ice water, and extracted three times with dichloromethane, an organic phase is collected, which is separated into silica gel, purified by a column chromatography (dichloromethane:n-hexane v:v, 3:2) to obtain 1.5 g deep red powders, and a yield is 48%.

1HNMR (300 MHz, $CD_2Cl_2$, δ): 8.74 (s, 4H), 7.21-7.13 (m, 12H), 6.97-6.88 (m, 4H).

MS (EI) m/z: $[M]^+$ calcd for $C_{36}H_{20}N_8S_2$, 628.13; found, 628.10.

Figure 2:
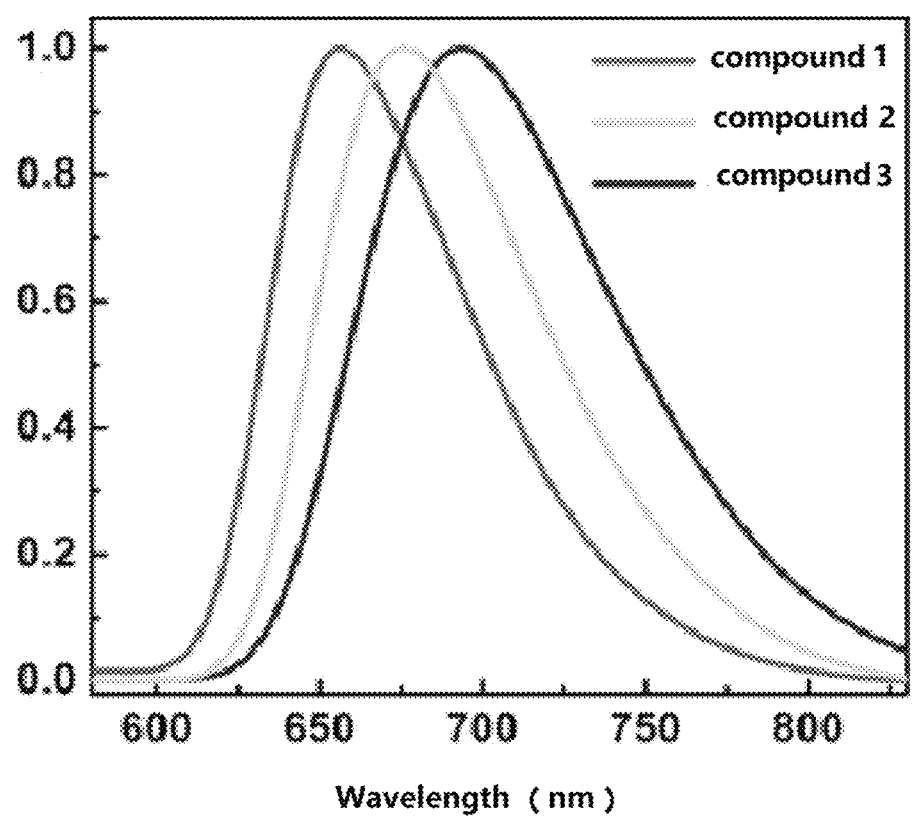
FIG. 2 is a photoluminescence spectrum of compounds 1-3 manufactured by exemplary embodiments 1-3 of the application in n-hexane solution at a room temperature.

FIG. 1 shows an orbital distribution spectrum of compounds 1-3, FIG. 1 introduces that, the highest occupied molecular orbitals (HOMOs) and the lowest unoccupied molecular orbitals (LUMOs) of the compounds 1-3 are distributed in different units to achieve a completely separation, thereby to decrease intersystem energy level difference ($\Delta E_{ST}$), and to promote a reverse intersystem crossing ability. FIG. 2 shows a photoluminescence spectrum of compounds 1-3 in n-hexane solution at a room temperature. For compounds 1-3, the lowest singlet energy level S1 and the lowest triplet energy level T1 of the molecule are simulated.

The relevant data of embodiments 1-3 is shown in Table 1. Table 1 introduces that, $\Delta E_{ST}$ of all of the compounds are less than 0.3 eV, thereby to achieve a small lowest single triple energy level difference and a significant delayed fluorescence effects.

TABLE 1 photophysical properties of compounds 1-3

| | PL Peak (nm) | S1 (eV) | T1 (eV) | $\Delta E_{ST}$ (eV) | HOMO (eV) | LUMO (eV) |
|---|---|---|---|---|---|---|
| Compound 1 | 659 | 1.88 | 1.71 | 0.17 | −5.18 | −2.53 |
| Compound 2 | 676 | 1.84 | 1.68 | 0.16 | −5.11 | −2.55 |
| Compound 3 | 693 | 1.79 | 1.66 | 0.13 | −5.12 | −2.54 |

In Table 1, PL Peak is photoluminescence peak, S1 is the singlet energy level, T1 is the triplet energy level, and $\Delta E_{ST}$ is the singlet and triplet energy level difference.

Embodiment 4

Manufacturing an organic light-emitting diode device:

Referring to FIG. 1, the organic light-emitting diode device having a light emitting layer containing the thermal active delay fluorescent material of the application used as an object material includes a substrate 9, a anode layer 1, a hole injection layer 2, a hole transport layer 3, a light emitting layer 4, an electron transport layer 5, and a cathode layer 6 formed from bottom to top. The substrate 9 is a glass substrate, a material of the anode 1 is indium tin oxide (ITO), the substrate 9 and the anode 1 are combined together to form a ITO glass, a square resistance of the ITO glass is 10 $\Omega/cm^2$. A material of the hole injection layer 2 is HATCN, a material of the hole transport layer 3 is TCTA, a material of the light emitting layer is a mixture of the thermal active delay fluorescent material of the application and mCBP, a material of the electron transport layer 5 is TmPyPB, the cathode is a double layer structure of a lithium fluoride (LiF) layer and an aluminium layer.

HCTCN is 2,3,6,7,10,11-hexacyano-1,4,5,8,9,12-hexaazatriphenylene, TCTA is 4,4',4"-tris(carbazol-9-yl)-triphenylamine, mCBP is 3,3'-Bis(N-carbazolyl)-1,1'-biphenyl, and TmPyPB is 1,3,5-tri[(3-pyridyl)-phen-3-yl] benzene.

Figure 3:
FIG. 3 is a structural spectrum of an organic light-emitting diode device of the application.

The organic light-emitting diode device can be manufactured by a manufacturing process of the prior art, and the manufacturing process is: on a cleaned ITO glass, a HATCN film with a 2 nm thickness, a TCTA film with a 35 nm thickness, mCBP combined with activation retardation fluorescent compound, a TmPyPB film with a 40 nm thickness, a LiF film with a 1 nm thickness and an Al film with a 100 nm thickness are sequentially deposited by a high vacuum condition. The manufacturing process manufactures a device shown as FIG. 3, device structures are as follows:

Device 1:
ITO/HATCN(2 nm)/TCTA(35 nm)/mCBP: compound 1 (5%, 40 nm)/TmPyPB (40 nm)/LiF(1 nm)/Al(100 nm)

Device 2:
ITO/HATCN(2 nm)/TCTA(35 nm)/mCBP: compound 2 (5%, 40 nm)/TmPyPB (40 nm)/LiF(1 nm)/Al(100 nm)

Device 3:
ITO/HATCN(2 nm)/TCTA(35 nm)/mCBP: compound 3 (5%, 40 nm)/TmPyPB (40 nm)/LiF(1 nm)/Al(100 nm)

Current-brightness-voltage characteristics of devices 1-3 are performed by a Keithley source measurement system (Keithley 2400 Sourcemeter, Keithley 2000 Currentmeter) with a calibrated silicon photodiode. The electroluminescence spectrums are measured by the French JY SPEX CCD3000 spectrometer. All measurements are done at a room temperature in atmosphere. Performance data for devices 1-3 is shown in Table 2.

TABLE 2 performance data of devices based on compounds 1-3 as object materials of the light-emitting layer

| Device | Maximum current efficiency (cd/A) | CIEy | Maximum external quantum efficiency (%) |
|---|---|---|---|
| Device 1 | 34.1 | 0.65 | 23.1 |
| Device 2 | 26.4 | 0.68 | 20.2 |
| Device 3 | 18.5 | 0.71 | 16.9 |

In the Table 2, CIEy is a y coordinate value of a standard CIE color space.

In conclusion, the application adopts a strong electron-withdrawing group of a large conjugate plane as an electron acceptor, and combines an electron acceptor with a strong electron donor to achieve a deep red light thermal active delay fluorescent material with a typical TADF characteristics and a low energy level, and using 100% internal quantum utilization efficiency of the TADF material, the thermal active delay fluorescent material used as the light emitting material is used in the organic light-emitting diode device to promote a luminous efficiency of the organic light-emitting diode device, the organic light-emitting diode device with the deep red light thermal active delay fluorescent material of the application achieves a very high device efficiency.

The above embodiments are preferred embodiments of the present invention, but the embodiments of the present invention are not limited to the above embodiments, and any other changes, modifications, substitutions, combinations, and combinations thereof may be made without departing from the spirit and scope of the invention. Simplifications should all be equivalent replacements and are included in the scope of the present invention.

What is claimed is:

1. A thermal active delay fluorescent material comprising a structural formula in formula 1:

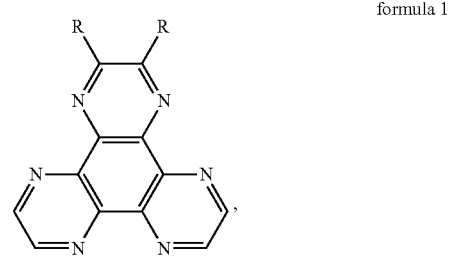

formula 1 wherein in the formula 1, R is a chemical group of an electron donor.

2. The thermal active delay fluorescent material of claim 1, wherein the chemical group R of the electron donor is one of:

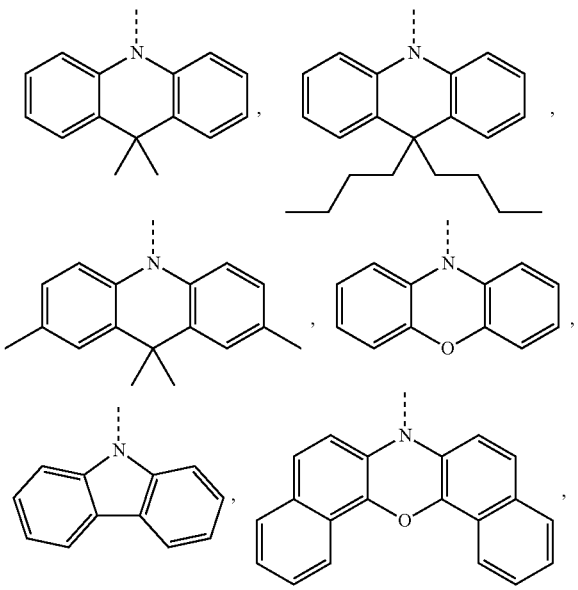

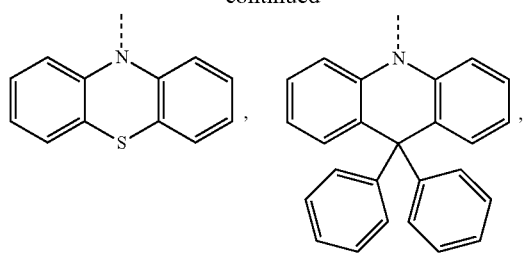
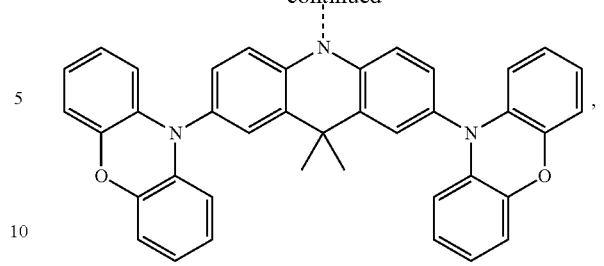
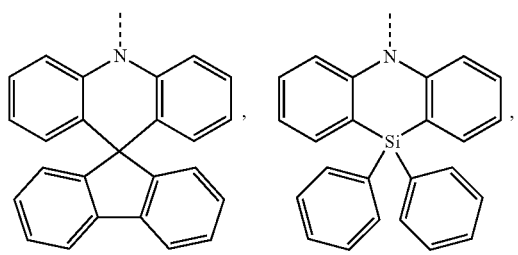
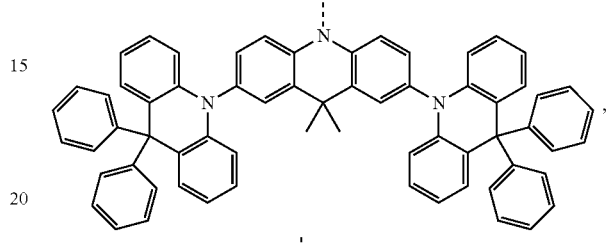
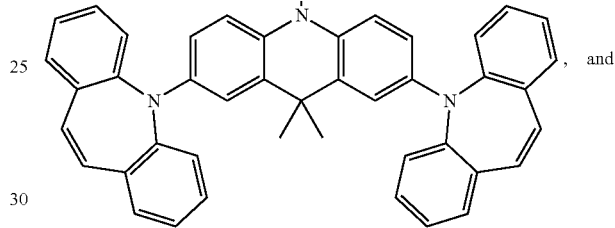
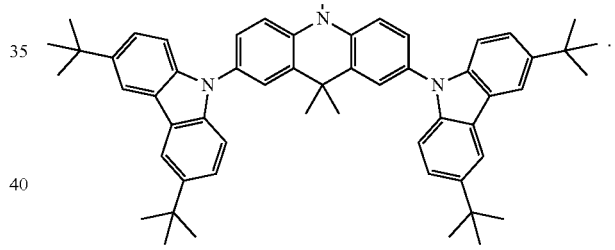
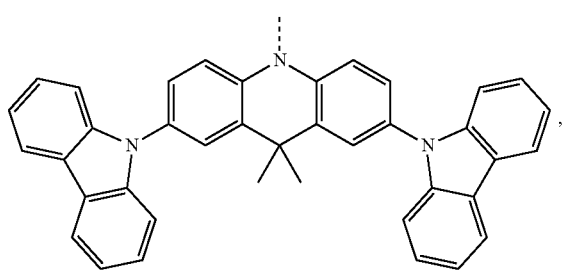
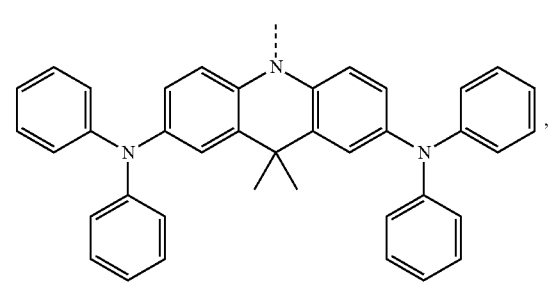
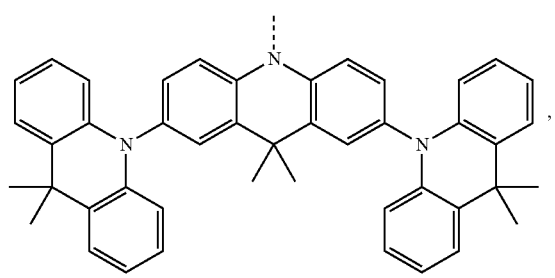
3. The thermal active delay fluorescent material of claim 2, wherein the thermal active delay fluorescent material is a compound 1, a compound 2, or a compound 3, structural formulas of the compound 1, the compound 2, and the compound 3 are defined as:
compound 1
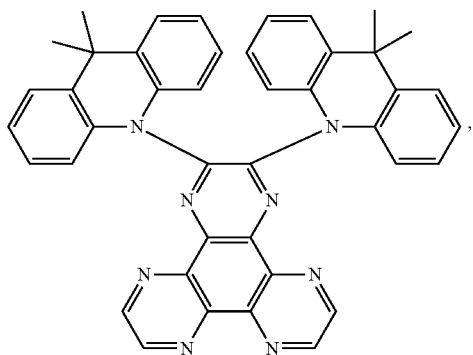

-continued compound 2

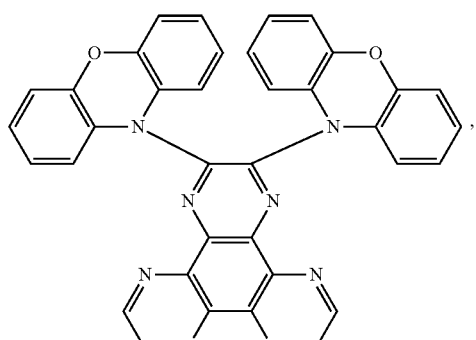

compound 3

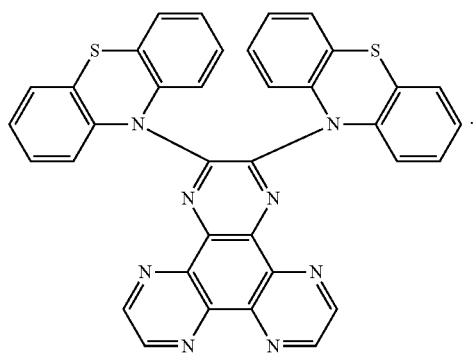

4. A method for manufacturing a thermal active delay fluorescent material, wherein a chemical equation is:

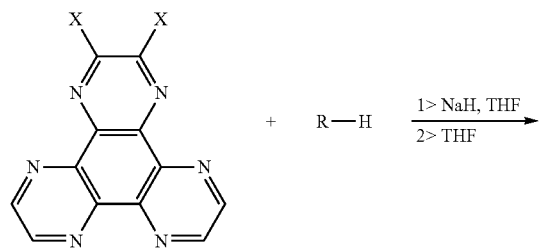

wherein a compound with an electron donor is added into a container, NaH is added into the container in an anhydrous and oxygen-free environment, dehydrogenation and deoxygenation of tetrahydrofuran is added into the container in an argon atmosphere, those are reacted at 55° C.-65° C. for 1.5-2.5 hours, and a halogenated material is added into the container, and then those are reacted at 55° C.-65° C. for 20-30 hours, wherein a molar ratio of the halogenated material, the compound with the electron donor, and NaH is 1:2-4: 2-4; after the reaction is completed, the reacted liquid is cooled to room temperature, poured into ice water, after a extraction process, an organic phase is collected, which is separated into silica gel, purified by a column chromatography to obtain a product;

wherein a structural formula of the halogenated material is

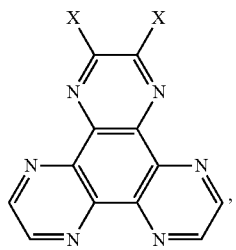

and X is a halogen group; a structural formula of the compound with the electron donor is R—H, and R is a chemical group of the electron donor.

5. The method for manufacturing a thermal active delay fluorescent material of claim 4, wherein the structural formula of the halogenated material is

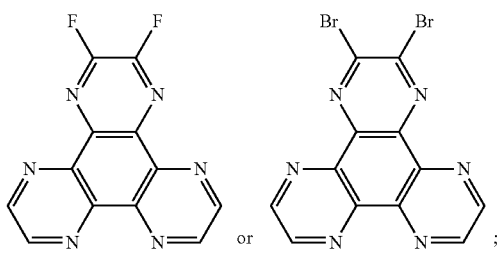

wherein the chemical group R of the electron donor is one of:

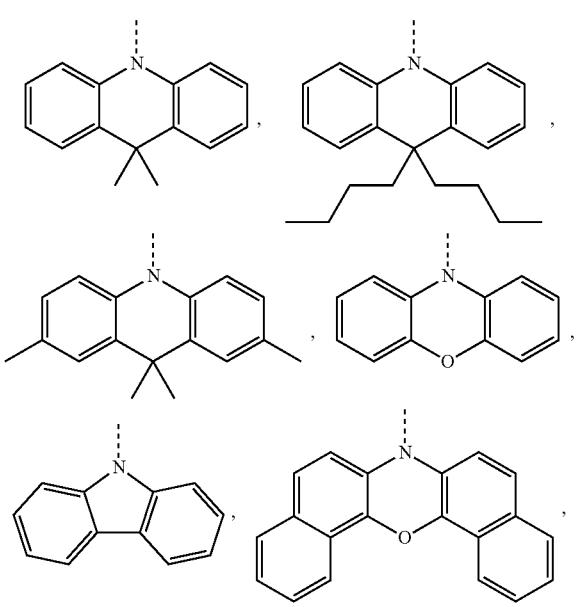

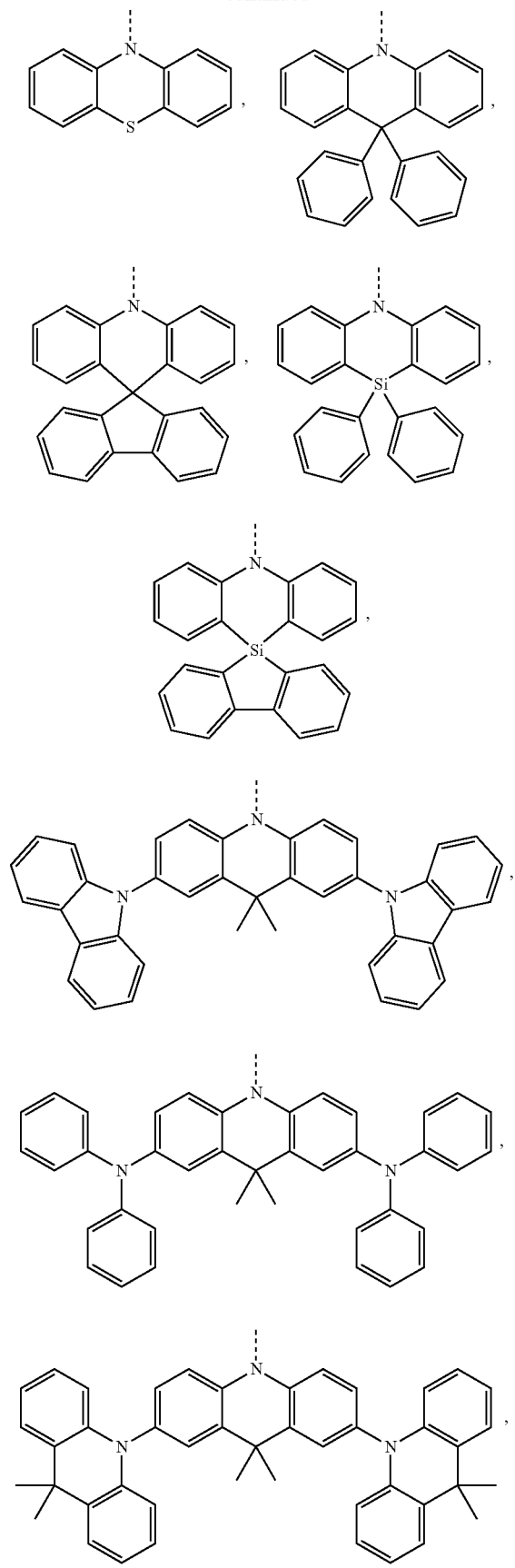

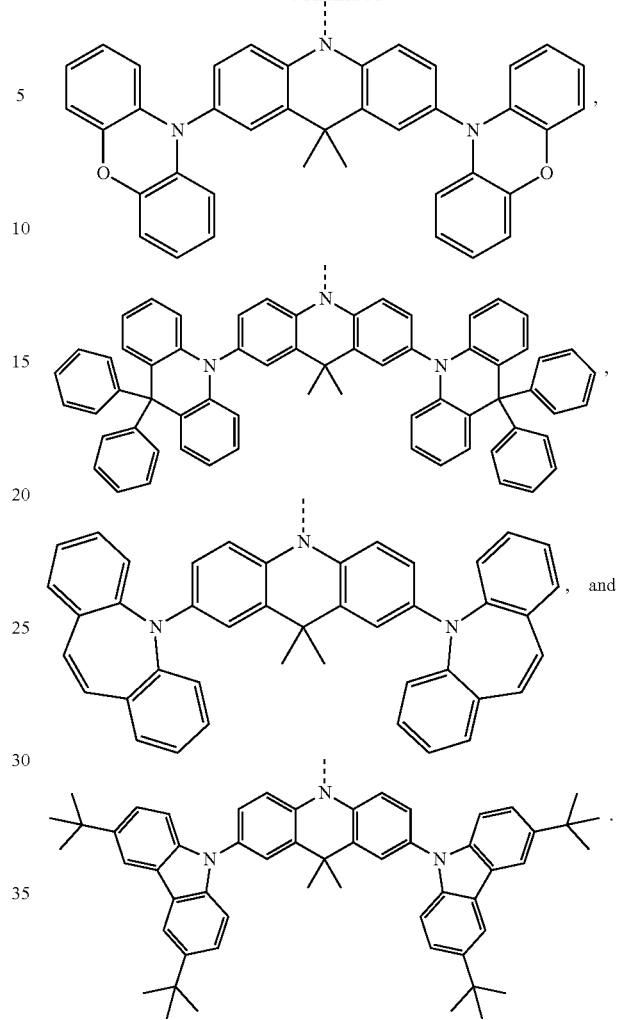

6. The method for manufacturing a thermal active delay fluorescent material of claim 5, wherein the compound with the electron donor is 9,10-dihydro-9,9-dimethyl acridine, phenoxazine, or phenothiazine.

7. An organic light-emitting diode device, wherein comprising a substrate, a first electrode formed on the substrate, an organic functional layer formed on the first electrode, and a second electrode formed on the organic functional layer; wherein the organic functional layer comprises one layer or several layers of organic film layers and at least one layer of the organic film layer is a light emitting layer; the light emitting layer comprises a thermal active delay fluorescent material of claim 1.

8. The organic light-emitting diode device of claim 7, wherein the light emitting layer is manufactured by a vacuum evaporation process or a coating solution process.

9. The organic light-emitting diode device of claim 7, wherein a material of the light emitting layer is a mixture of a subject material and an object material, the object material is selected one or several from the thermal active delay fluorescent material of claim 7.

10. The organic light-emitting diode device of claim 9, wherein the substrate is a glass substrate, a material of the first electrode is indium tin oxide, the second electrode is a double layer composite structure of a lithium fluoride layer and an aluminum layer;

the organic functional layer comprises several layers of the organic film layers, the several layers of the organic film layers comprises a hole injection layer, a hole transport layer, a luminescence layer, and an electron transport layer, wherein a material of the hole injection layer is 2,3,6,7,10,11-hexacyano-1,4,5,8,9,12-hexaaza-triphenylene (HATCN), a material of the hole transport layer is 4,4',4"-tris(carbazol-9-yl)-triphenylamine (TCTA), a material of the electron transport layer is 1,3,5-tri[(3-pyridyl)-phen-3-yl]benzene (TmPyPB), and the subject material is 3,3'-Bis(N-carbazolyl)-1,1'-biphenyl (mCBP).

* * * * *